(12) United States Patent
Simanovsky et al.

(10) Patent No.: US 9,633,428 B2
(45) Date of Patent: Apr. 25, 2017

(54) AUTOMATIC OCCLUSION REGION IDENTIFICATION USING RADIATION IMAGING MODALITY

(75) Inventors: Sergey Simanovsky, Brookline, MA (US); Ram Naidu, Newton, MA (US)

(73) Assignee: Analogic Corporation, Peabody, MA (US)

( * ) Notice: Subject to any disclaimer, the term of this patent is extended or adjusted under 35 U.S.C. 154(b) by 56 days.

(21) Appl. No.: 14/408,283

(22) PCT Filed: Jun. 29, 2012

(86) PCT No.: PCT/US2012/044869
§ 371 (c)(1),
(2), (4) Date: Dec. 15, 2014

(87) PCT Pub. No.: WO2014/003782
PCT Pub. Date: Jan. 3, 2014

(65) Prior Publication Data
US 2015/0139491 A1  May 21, 2015

(51) Int. Cl.
*G06K 9/00* (2006.01)
*G01N 23/04* (2006.01)
(Continued)

(52) U.S. Cl.
CPC .......... *G06T 7/0006* (2013.01); *G01N 23/046* (2013.01); *G01V 5/005* (2013.01);
(Continued)

(58) Field of Classification Search
USPC ........ 382/100, 103, 106–108, 128–132, 151, 382/155, 162, 168, 173, 181, 190–199,
(Continued)

(56) References Cited

U.S. PATENT DOCUMENTS 6,195,444 B1  2/2001  Simanovsky et al.
6,345,113 B1 *  2/2002  Crawford ........... G06K 9/00201
378/57

(Continued)

FOREIGN PATENT DOCUMENTS

JP  2003516517 A  5/2003

OTHER PUBLICATIONS

International Search Report cited in related application No. PCT/US12/44869 dated Nov. 8, 2012, pp. 16.
(Continued)

*Primary Examiner* — Seyed Azarian
(74) *Attorney, Agent, or Firm* — Cooper Legal Group LLC

(57) ABSTRACT

Among other things, one or more systems and/or techniques for identifying an occlusion region in an image representative of an object subjected to examination is provided for herein. Such systems and/or techniques may find particular application in the context of object recognition analysis. An image is generated of the object and an orientation of the object is determined from the image. Based upon the determined orientation of the object relative to the direction the object is translated during examination, one or more parameters utilized for segmenting a second image of the object, identifying features in the image, and/or determining if the image comprises an occlusion region may be adjusted. In this way, the parameters utilized may be a function of the determined orientation of the object, which may mitigate false positives of detected occlusion regions.

20 Claims, 5 Drawing Sheets

(51) Int. Cl.
*G06T 7/00* (2017.01)
*G01V 5/00* (2006.01)

(52) U.S. Cl.
CPC .......... *G06T 7/0004* (2013.01); *G06T 7/0012* (2013.01); *G06T 7/0081* (2013.01); *G06T 2207/10081* (2013.01); *G06T 2207/20148* (2013.01); *G06T 2207/30112* (2013.01)

(58) Field of Classification Search
USPC ................ 382/209, 219, 232, 254, 274–276, 382/284–291, 305, 312, 170; 378/57; 436/57
See application file for complete search history.

(56) References Cited

U.S. PATENT DOCUMENTS

| | | | |
|---|---|---|---|
| 2006/0056727 A1* | 3/2006 | Jones | G06K 9/32 382/276 |
| 2007/0014471 A1* | 1/2007 | Simanovsky | G01T 1/2985 382/170 |
| 2007/0014472 A1* | 1/2007 | Ying | G01V 5/0041 382/170 |
| 2008/0014643 A1* | 1/2008 | Bjorkholm | G01N 23/04 436/57 |
| 2008/0193002 A1* | 8/2008 | Ying | G01V 5/0008 382/131 |

OTHER PUBLICATIONS

Singh, et al., "Explosives detection systems (EDS) for aviation security", Signal Processing, Elsevi er Science Publishers B.V. Amsterdam, NL, vol. 83, No. 1, Jan. 1, 2003 (Jan. 1, 2003), pp. 31-55. XP027139545. ISSN: 0165-1684 [retrieved on Jan. 1, 2003] Section IIDual-energy X-ray; p. 35-p. 37 p. 39 Section "3D X-ray imaging (a) Computed tomography" ; p. 40-p. 41 Section 3.1.

Korean Office Action cited in Japanese Application No. 20156-520144 dated Mar. 1, 2016, 2 pgs.

EP Communication cited in EP Application No. 12 735 070.0 dated Feb. 14, 2017, 3 pgs.

* cited by examiner

AUTOMATIC OCCLUSION REGION IDENTIFICATION USING RADIATION IMAGING MODALITY

BACKGROUND

The present application relates to the field(s) of X-ray and computed tomography (CT). It finds particular application with security systems configured to image an object, segment the image and resultantly identify one or more potential occlusion regions within the object, where such occlusion regions may contain one or more threat items. It also relates to medical, industrial, and/or other applications where identifying sub-objects within an object presently and/or previously under examination would be useful.

Security at airports and/or in other travel related areas is an important issue given today's sociopolitical climate, as well as other considerations. One technique used to promote travel safety is baggage inspection via a radiation imaging modality. For example, a CT system may be used to provide security personnel with two and/or three dimensional views of objects. After viewing images provided by the imaging apparatus, security personnel may make a decision as to whether the baggage is safe to pass through a security check-point or if further (hands-on) inspection is warranted.

To reduce human error that may be associated with identifying potential threat items inside baggage, automated object recognition systems may be utilized. Such systems can segment (e.g., extract) a sub-object from an image, and compute properties of the sub-object. Computed properties of the sub-object can then be used for discriminating a sub-object by comparing the sub-object's properties (e.g., density, effective atomic number, shape, etc.) with known properties of threat items, non-threat items, and/or both classes of items, etc., for example.

U.S. Pat. No. 6,345,113, assigned to Analogic Corporation and incorporated herein by reference, describes one approach for object recognition. Among other things, as part of the process, regions of the object under examination that are occluded due to the presence of highly attenuating sub-objects may be identified in a two-dimensional projection image representative of the object. Because such regions attenuate substantially all of the radiation impinging thereon, it is difficult to generate/reconstruct an image that provides sufficient information from which to identify one or more sub-objects disposed within the occlusion region. As such, an alert may be issued to security personnel notifying the personnel about the lack of information and requesting that the security personnel perform a more detailed (hands-on) inspection of the object.

Conventionally, to identify an occlusion region (e.g., a region representing one or more occluded sub-objects) of a two-dimensional projection image, one or more values (e.g., CT values, z-effective values, etc.) associated with respective pixels of the image (or merely of pixels associated with a potential occlusion region) are compared to predetermined, fixed parameters. Thus, an occlusion region may be defined as comprising pixels respectively associated with a value that corresponds to predetermined parameters for an occlusion region. Typically, an assumption made when pre-defining parameters for an occlusion region is that the object (e.g., suitcase) is oriented such that a long axis of the object is parallel with a direction of conveyance of the object during examination.

With the advent of wide-area bores in CT systems and automatic object feeders (e.g., configured to automatically feed objects onto a conveyor belt of the imaging modality), some objects may be oriented, however, such that the long axis is not parallel to the direction of conveyance. As such, the predefined parameters may be inaccurate given the orientation of the object, resulting in false identifications of occlusion regions.

SUMMARY

Aspects of the present application address the above matters, and others. According to one aspect an imaging apparatus for automatic occlusion detection is provided. The apparatus comprises an orientation component configured to determine an orientation of an object from a first image representative of the object. The apparatus also comprises a segmentation component configured to segment a second image representative of the object to generate a segmented image based upon one or more segmentation parameters, at least one of the one or more segmentation parameters dynamically adjusted as a function of the determined orientation of the object. The apparatus further comprises a feature extraction component configured to identify, from the segmented image, a potential occlusion region in the second image.

According to another aspect, a method for segmenting an image to identify a potential occlusion region in the image is provided. The method comprises determining an orientation of an object from a first image representative of the object. The method also comprises segmenting, using one or more segmentation parameters, a second image representative of the object to generate a segmented image, indicative of a potential occlusion region, at least one of the one or more segmentation parameters dynamically adjusted as a function of the determined orientation of the object.

According to another aspect, a computer readable medium comprising processor-executable instructions that when executed via a processing unit perform a method for automatic occlusion detection is provided. The method comprises determining an orientation of an object from a first image representative of the object. The method also comprises segmenting, using one or more segmentation parameters, a second image representative of the object to generate a segmented image, indicative of a potential occlusion region, at least one of the one or more segmentation parameters dynamically adjusted as a function of the determined orientation of the object.

Those of ordinary skill in the art may appreciate still other aspects of the present application upon reading and understanding the appended description.

FIGURES

The application is illustrated by way of example and not limitation in the figures of the accompanying drawings, in which like references generally indicate similar elements and in which.

DESCRIPTION

Figure 1:
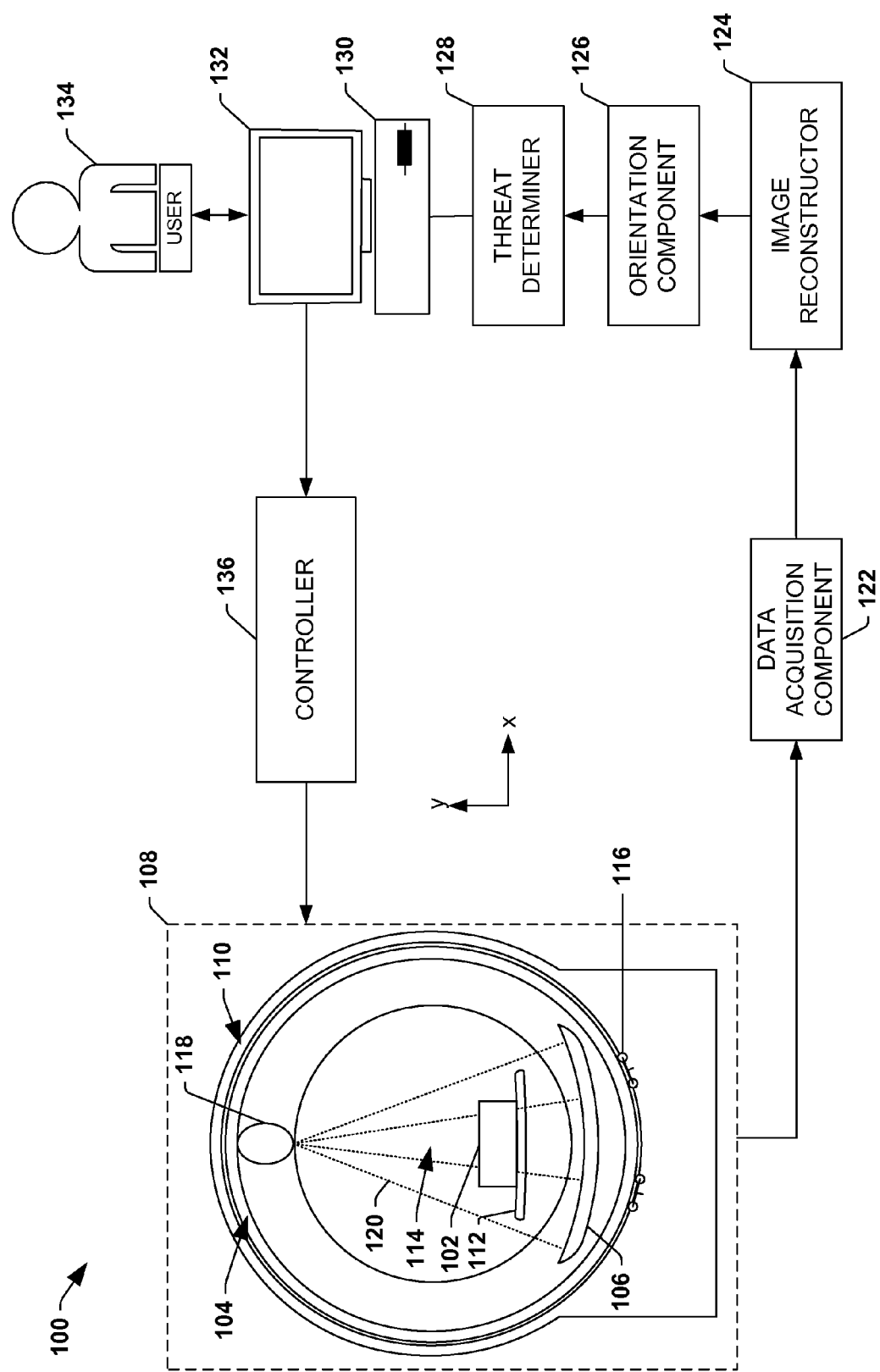
FIG. 1 illustrates an example environment of an imaging modality.

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are illustrated in block diagram form in order to facilitate describing the claimed subject matter.

Among other things, one or more systems and/or techniques for identifying potential occlusion regions in an image of the object are provided for herein. Typically, the object is examined via a radiation imaging modality, such as a CT scanner and/or a line scanner, for example, and one or more images are generated from the examination. Using the image(s), an orientation of the object (e.g., relative to a conveyor belt or other support article supporting the object in an examination region) is determined. For example, Eigen analysis may be performed on the image to identify Eigen vectors for the object. Once the orientation of the object is determined, one or more parameters utilized for identifying an occlusion region may be dynamically adjusted. For example, segmentation parameters (e.g., utilized for identifying/segmenting a potential occlusion region), feature extraction parameters (e.g., utilized for identifying/determining features of the occlusion region and/or of a sub-object(s) represented by the region), and/or discrimination parameters (e.g., utilized for assessing whether a potential occlusion region is indeed an occlusion region) may be dynamically adjusted based upon the determined orientation of the object. In this way, object recognition (e.g., threat detection) algorithms, for example, may be adjusted to account for the orientation of an object being examined, for example.

FIG. 1 is an illustration of an example environment 100 comprising a computed tomography (CT) system that may be configured to generate images representative of an object 102 (e.g., baggage, patient, etc.) or aspect(s) thereof under examination and to perform object recognition analysis on the generated image(s). Such an example system may be employed for identifying potential threat containing objects, from a class of objects, inside baggage that has been subjected to imaging, for example.

It may be appreciated that while the example environment 100 describes a CT system configured to generate two-dimensional and/or three-dimensional images of the object 102 under examination (or previously under examination), other radiation imaging modalities are also contemplated for generating images from which object recognition analysis may be performed. For example, line systems and/or projection systems may be utilized to generate two-dimensional images from which object recognition analysis may be performed. Moreover, the arrangement of components and/or the types of components included in the example environment 100 are merely provided as an example arrangement. By way of example, in another embodiment, the data acquisition component 122 may be comprised within the detector array 106.

In the example environment 100, an examination unit 108 of the CT system is configured to examine one or more objects 102. The examination unit 108 can comprise a rotating gantry 104 and a (stationary) support structure 110 (e.g., which may encase and/or surround at least a portion of the rotating gantry 104 (e.g., as illustrated with an outer, stationary ring, surrounding an outside edge of an inner, rotating ring)). During an examination of the object(s) 102, the object(s) 102 can be placed on a support article 112, such as a bed or conveyor belt, for example, that is selectively positioned in an examination region 114 (e.g., a hollow bore in the rotating gantry 104), and the rotating gantry 104 can be rotated and/or supported about the object(s) 102 by a rotator 116, such as a motor, drive shaft, chain, roller truck, etc.

The rotating gantry 104 may surround a portion of the examination region 114 and may comprise one or more radiation sources 118 (e.g., an ionizing x-ray source, gamma radiation source, etc.) and a detector array 106 that is mounted on a substantially diametrically opposite side of the rotating gantry 104 relative to the radiation source(s) 118.

During an examination of the object(s) 102, the radiation source(s) 118 emits fan, cone, wedge, and/or other shaped radiation 120 configurations from a focal spot(s) of the radiation source(s) 118 (e.g., a region within the radiation source(s) 118 from which radiation 120 emanates) into the examination region 114. It may be appreciated that such radiation 120 may be emitted substantially continuously and/or may be emitted intermittently (e.g., a brief pulse of radiation is emitted followed by a resting period during which the radiation source 118 is not activated).

As the emitted radiation 120 traverses the object(s) 102, the radiation 120 may be attenuated differently by different aspects of the object(s) 102. Because different aspects attenuate different percentages of the radiation 120, an image(s) may be generated based upon the attenuation, or variations in the number of photons that are detected by the detector array 106. For example, more dense aspects of the object(s) 102, such as a bone or metal plate, may attenuate more of the radiation 120 (e.g., causing fewer photons to strike the detector array 106) than less dense aspects, such as skin or clothing.

The detector array 106 is configured to directly convert (e.g., using amorphous selenium and/or other direct conversion materials) and/or indirectly convert (e.g., using photo-detectors and/or other indirect conversion materials) detected radiation into signals that can be transmitted from the detector array 106 to a data acquisition component 122 configured to compile signals that were transmitted within a predetermined time interval, or measurement interval, using various techniques (e.g., integration, photon counting, etc.). It may be appreciated that such a measurement interval may be referred to as a "view" and generally reflects signals generated from radiation 120 that was emitted while the radiation source 118 was at a particular angular range relative to the object 102. Based upon the compiled signals, the data acquisition component 122 can generate projection data indicative of the compiled signals, for example, and the compilation of projection data from a plurality of views may cause volumetric data to be generated from the examination.

The example environment 100 further comprises an image reconstructor 124 configured to receive the projection data that is output by the data acquisition component 122. The image reconstructor 124 is configured to generate image data (also referred to as images) from the projection data using a suitable analytical, iterative, and/or other reconstruction technique (e.g., backprojection reconstruction, tomosynthesis reconstruction, iterative reconstruction, etc.). In this way, the data is converted from projection space to image space, a domain that may be more understandable by a user 134 viewing the image(s), for example. It may be appreciated that, in a CT context, the images generated by the image reconstructor 124 may be two dimensional images and/or three-dimensional images, for example.

In the example environment 100, an orientation component 126 may be configured to receive the image data and to determine an orientation of the object 102 relative to a direction the object 102 traveled during the examination via the support article 112, for example. By way of example, in one embodiment, the orientation component 126 is configured to receive an image (e.g., such as a two-dimensional image representing the object in a plane) from the image reconstructor 124 and is configured to determine an orientation of the object 102 using suitable analytical, iterative, and/or other orientation determining techniques. For example, in one embodiment, an Eigen analysis may be performed on the image to determine principal axes of the object 102 as represented in the image.

The example environment 100 further comprises a threat determiner 128 configured to perform object recognition analysis, where one or more parameters utilized for the analysis is a function of the determined orientation of the object 102. For example, as will be described in more detail below, the threat determiner 128 may be configured to, among other things, segment one or more images to generate a segmented image(s) (where respective segments are representative of one or more sub-objects comprised within the object 102), identify a potential occlusion region in the segmented image(s), identify one or more features of the potential occlusion region, and/or compare the identified one or more features to discrimination parameters/thresholds to confirm the presence of an occlusion region. When the identified one or more features satisfy the discrimination parameters, for example, the potential occlusion region may be labeled as an occlusion region and an alert may be issued to a terminal 130, for example, notifying a user 134 that further (hands-on) inspection may be warranted.

It may be appreciated that identification of an occlusion region may be one of numerous functions that the threat determiner 128 is configured to perform. For example, when no occlusion region is identified in an image, the threat determiner 128 may be configured to perform automatic threat detection on the image data to identify one or more potential threat objects represented in the image, and to output information indicative of whether a potential threat item(s) has been identified based upon the comparison, for example. Thus, in such an embodiment, determining whether an image comprises an occlusion region is merely a preliminary action to determine whether image data comprises sufficient information from which to identify potential threat objects (e.g., where the identification of an occlusion region indicates that, in at least a portion of the image, insufficient information may exist from which to rule out potential threat objects).

It may also be appreciated that although the component configured to perform object recognition is labeled as a threat determiner 128, such a component may be configured to identify other, non-threat items. For example, in a medical application, the threat determiner 128 may be configured to identify particular aspects of a patient under examination such as desired bones, organs, and/or other physical structures. As another example, in an industrial application, the threat determiner 128 may be configured to identify knots in timber being examined, for example. Thus, despite the terminology "threat determiner," the threat determiner 128 may be configured to identify non-threating aspects of an object 102 under examination.

The example environment 100 further comprises a terminal 130, or workstation (e.g., a computer), that may be configured to receive the image data (e.g., output by the image reconstructor 124, the orientation component 126, and/or the threat determiner 128) and/or other information, such as alerts, output by the threat determiner 128. The terminal 130 may also be configured to present the image data and/or information for display on a monitor 132 to a user 134 (e.g., security personnel, medical personnel, etc.). In this way, the user 134 can inspect the image(s) to identify areas of interest within the object(s) 102. The terminal 130 can also be configured to receive user input which can direct operations of the object examination apparatus 108 (e.g., a speed to rotate, a speed of a conveyor belt, etc.), for example.

In the example environment 100, a controller 136 is operably coupled to the terminal 130. In one example, the controller 136 is configured to receive input from the terminal 130, such as user input for example, and to generate instructions for the object examination apparatus 108 indicative of operations to be performed. For example, the user 134 may desire to reexamine the object(s) 102 at a different energy level, and the controller 136 may issue a command instructing the support article 112 to reverse direction (e.g., bringing the object(s) 102 back into an examination region 114 of the object examination apparatus 102).

It may be appreciated that the example component diagram is merely intended to illustrate one embodiment of one type of imaging modality and is not intended to be interpreted in a limiting manner. For example, the functions of one or more components described herein may be separated into a plurality of components and/or the functions of two or more components described herein may be consolidated into merely a single component. Moreover, the imaging modality may comprise additional components configured to perform additional features, functions, etc. and/or some components described herein may be optional.

Figure 2:
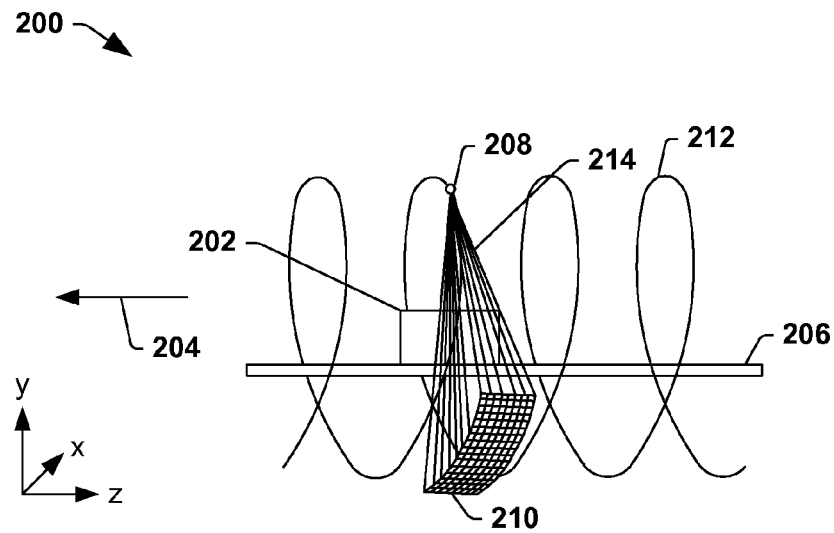
FIG. 2 illustrates a functional diagram of a helical scan performed via a CT imaging modality.

FIG. 2 is a functional diagram 200 of a helical scan performed via a CT imaging modality, such as in security and/or medical applications. In such an imaging modality, an object 202 (e.g., 102 in FIG. 1) under examination is translated 204 (e.g., at a constant speed, in a step- and shoot manner, etc.) in a direction parallel to an axis of rotation (e.g., along a z-axis), via an object support 206 (e.g., 112 in FIG. 1). The object 202 is exposed to radiation 214 while the object 202 is being translated and/or between translations. That is, one or more radiation sources 208 (e.g., 118 in FIG. 1) are configured to emit radiation 214, causing the object 202 to be exposed to radiation 214. A detector array 210 (e.g., 106 in FIG. 1), mounted on a substantially diametrically opposite side of the object 202 relative to the radiation source(s) 208, is configured to detect radiation 214 that has traversed the object 202. In this way, by emitting and detecting radiation 214, the object 202 is examined.

In a CT imaging modality, the radiation source(s) 208 and the detector array 210 are typically rotated about the object 202 (e.g., in an x-y plane) via a rotating gantry (e.g., 104 in FIG. 1) during the examination. Thus, in an environment where the object 202 is translated at a substantially constant speed, such a rotation may cause the radiation source(s) 208 and/or the detector array 210 to follow a spiral or helical-like trajectory 212 relative to the object (e.g., where the radiation source(s) 208 and detector array 210 do not move in the z-direction, and thus the helical trajectory is established by the combination of the x/y rotation of the source 208 and detector array 210 and the z-direction translation 204 of the object 202). As the object 202 is translated, data for a prescribed number of slices of the object 202 may be acquired via detected radiation 214.

Figure 3:
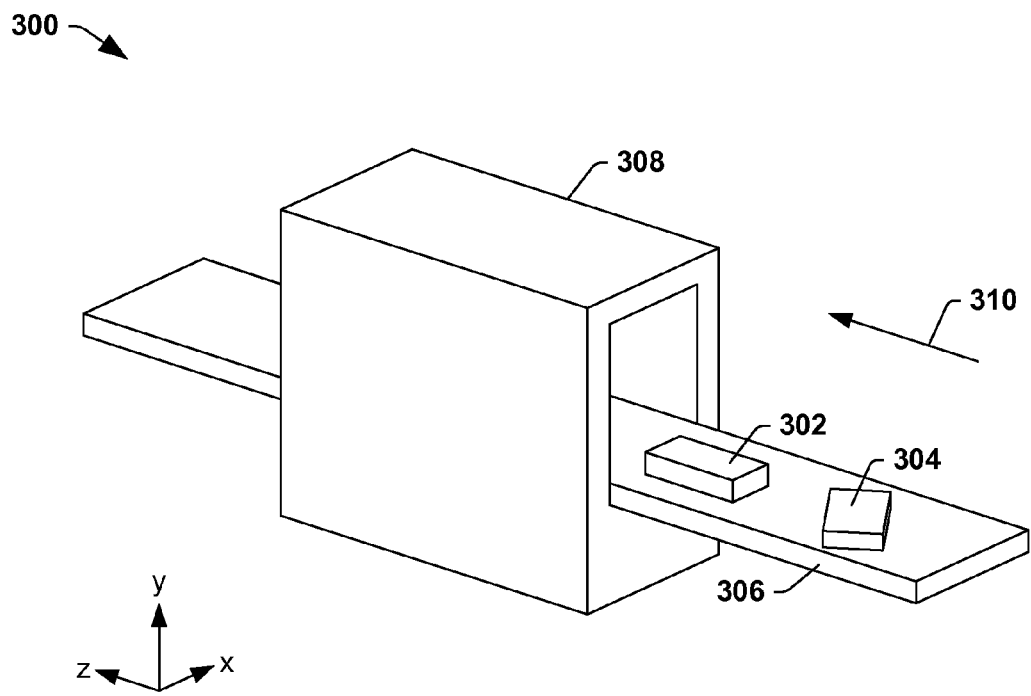
FIG. 3 illustrates an example system configured to examine one or more objects.

FIG. 3 illustrates an example system 300 (e.g., such as may be comprised within environment 100 in FIG. 1) configured to examine one or more objects 302, 304 (e.g., 202 in FIG. 2). By way of example, baggage may be examined at an airport or other security checkpoint via radiation before being permitted to enter a secure zone of the airport or other venue. In this way, security personnel may examine an image(s) representing the interior of the baggage for potential threat items.

The objects 302, 304 are translated or conveyed, via an object support 306 (e.g., 206 in FIG. 2), relative to a radiation source (e.g., 208 in FIG. 2) and/or a detector array (e.g., 210 in FIG. 2), which are enclosed by a member 308. As illustrated, the objects 302, 304 may be oriented in different ways relative to a direction 310 that the objects are conveyed via the object support 306. By way of example, a first object 302 is oriented such that its longitudinal axis (e.g., an axis parallel to the longest dimension of the object 302) is parallel to a direction of translation 310 (e.g., 204 in FIG. 2) (e.g., parallel to the z-axis) whereas a longitudinal axis of a second object 304 is turned approximately 45 degrees relative to the direction of translation 310.

Conventionally, some threat detection parameters (or more particularly parameters for identifying an occlusion region), such as segmentation parameters, feature extraction parameters, and/or discrimination parameters have been defined with the assumption that objects 302, 304 are at a particular orientation. For example, in security applications, such parameters may rely on baggage being oriented with the longitudinal axis of the baggage being approximately parallel to the direction of translation 310. When an object, such as the second object 304, is oriented differently, object recognition analysis may return incorrect/false results because the direction of the longitudinal axis of the second object 304 does not satisfy the assumption.

Thus, as provided for herein, the orientation of an object may be determined prior to threat detection (e.g., prior to examining the image for an occlusion region(s)), for example, and parameters utilized for threat detection may be dynamically adjusted according to the orientation of the object. That is, the type of properties (e.g., density, z-effective, Compton score, etc.) and/or the threshold value of such properties may be adjusted according to the determined orientation of the object. By way of example, parameters that are compared to an image representative of the first object 302 may be different than parameters that are compared to an image representative of the second object 304 because the objects 302, 304 are oriented differently. As such, it may be said that the parameters are at least partially defined as a function of a determined orientation of an object represented in an image being examined (e.g., for threat or other object recognition purposes).

Returning to FIG. 1, the orientation component 126 is configured to determine an orientation of an object from a first image representative of the object (e.g., received from the image reconstructor 124) using suitable analytic, iterative, or other techniques for determining object orientation from image data. By way of example, the orientation component 126 may be configured to perform an Eigen analysis on a two-dimensional projection image to determine Eigen vectors of the object (e.g., where at least one Eigen vector is indicative of the longitudinal axis of the object). It may be appreciated that although specific reference may be made to using a two-dimensional projection image, the orientation component 126 may be configured to determine the orientation of the object using various types of images that may be produced by a radiation imaging modality. For example, object orientation may be determined from a direct two-dimension image (e.g., a real projection), a re-projected three-dimensional image, and/or a three-dimensional image (e.g., where Eigen vectors of the three-dimensional image can be projected onto a two-dimensional plane). Further, the orientation component may be configured to utilize an optical image and/or other modified (two-dimensional or three-dimensional) image that is derivable from the data acquired from the detection of radiation.

It may be appreciated that Eigen vectors (e.g., principal axes) may be explained simply with regards to length and width when a two-dimensional plane of the object is viewed (e.g., or with regards to a length, width, and depth when the object is viewed in three-dimensions). Generally, a first principal axis is parallel to the longitudinal axis (e.g., the length or longest dimension) of the object. Because the Eigen vectors create a Cartesian coordinate system, the other principal axis of the object, as represented in the two-dimensional image being analyzed (e.g., or other principal axes of the object as represented in a three-dimensional image), may be determined based upon the identification of the first principal axis. It may be appreciated that the orientations of the principal axes do not vary relative to the object based upon the orientation of the object. For example, regardless of whether the longitudinal axis of a book is tilted at a 45 degree angle or at a 50 degree angle relative to the direction in which the object is translated (e.g., 310 in FIG. 3), the principal a-axis, for example, will have a same orientation relative to the object.

In one embodiment, prior to determining the orientation of the object using Eigen analysis or other techniques, the orientation component 126 may be configured to analyze the image to define a region of interest (ROI) or bounding box for the region of interest. Typically, the region of interest is defined as the region of the image representing the object under examination. Therefore, pixels representative of a conveyor belt, air, or other aspects that are not part of the object under examination may be eliminated, zeroed, etc. to reduce the amount of data that is analyzed when determining the orientation of the object, for example.

Figure 4:
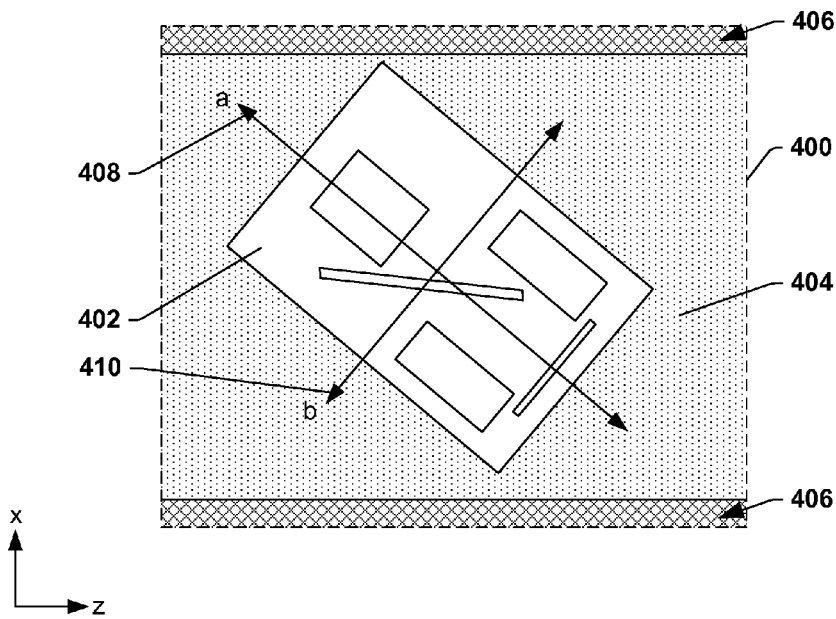
FIG. 4 illustrates an example two-dimensional image from which an orientation of an object may be determined.

FIG. 4 illustrates an example projection image 400 of an object 402 (e.g., 304 in FIG. 3) that may be received by an orientation component (e.g., 126 in FIG. 1) from an image reconstructor (e.g., 124 in FIG. 1), for example. Again, it may be appreciated that although specific reference is made herein to a two-dimensional projection image, other radiation (e.g., X-ray) images and/or non-radiation images derivable from detected radiation (e.g., such as an optical image) are also contemplated for use in determining an orientation of the object 402, for example.

In the illustrated embodiment, the projection image 400 is a top-down image depicting a plane of the image that is substantially parallel to a surface of an object support 404, such as conveyor belt, for example (e.g., represented by a dotted pattern). While a top-down image may be preferable for performing object orientation analysis, it may be appreciated that other image planes may be utilized for determining an orientation of the object (e.g., relative to the direction of translation). For example, a top-down image may illustrate the object 402 from the viewpoint of the radiation source when the radiation source is at a rotation angle of approximately 0 degrees. In another embodiment, the orientation component may utilize an image plane illustrating the object 402 from a viewpoint of the radiation source when the radiation source is at a rotation angle of approximately 20 degrees. Thus, an image may correspond to an image plane of the object 402 that is different than the top-down image plane illustrated in FIG. 4.

As described above, initially, the orientation component may filter the image 400 or define a region of interest within the image 400 to reduce the amount of image data that is analyzed when determining the orientation of the object 402. For example, in the illustrated embodiment, the portion of the image 400 representative of the object support 404 (e.g., as represented by the dotted pattern) and the portions of the image 400 representative of air 406 (e.g., the cross-hatched portions) may be discarded or otherwise ignored during the orientation analysis because such portions are not representative of the object 402.

The orientation component may be further configured to determine the orientation of the object 402 by performing an Eigen analysis on the remaining pixels of the image 400, for example, or by using other orientation analysis techniques. In this way, principal axes may be defined that describe the dimensions of the object 402. For example, by performing Eigen analysis on the projection image 400, it may be determined that a first principal axis 408 or Eigen vector is angled at substantially 45 degrees relative to the direction of translation (e.g., which is parallel to the z-axis). This first principal axis 408 may define the longitudinal axis or length of the object 402 (e.g., which has conventionally been oriented parallel to the direction of translation). A second principal axis 410 may be defined as an axis that intersects the first principal axis 408 at a substantially ninety degree angle. In this way, a two-dimensional projection image may be utilized to determine Eigen vectors that are indicative of an orientation of the object relative to a direction of translation, for example (e.g., although again other types of images may be utilized to find Eigen vectors and/or utilized to determine the orientation of the object).

Based upon the determined orientation of the object 402, one or more parameters utilized by a threat determiner (e.g., 128 in FIG. 1) when analyzing the object 402, or rather when determining if an image of the object 402 comprises an occlusion region, may be dynamically set and/or adjusted. In this way, algorithms for identifying occlusion regions in images of objects may be dynamically adjusted to account for differences in the orientation of objects that are conveyed through an examination unit (e.g., 108 in FIG. 1), for example, to reduce and/or mitigate false positives of occlusion regions.

Figure 5:
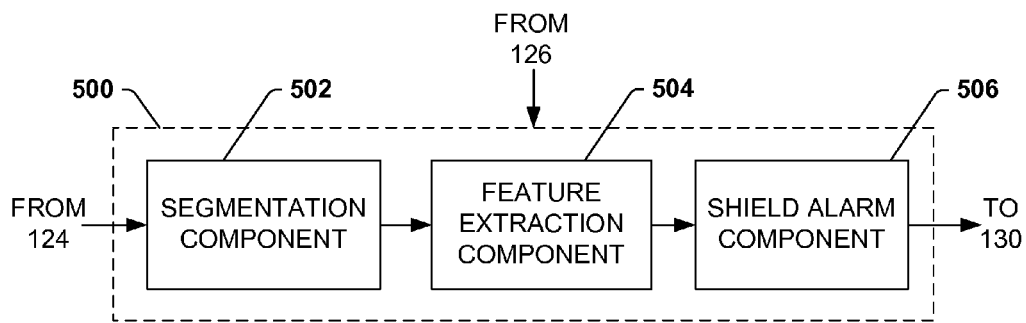
FIG. 5 illustrates a component block diagram of an example threat determiner.

FIG. 5 illustrates an example threat determiner 500 (e.g., 128 in FIG. 1) configured to, among other things, identify occlusion regions in an image indicative of highly attenuating sub-objects within an object under examination and/or to perform object recognition analysis on the image (e.g., when no occlusion regions are identified). In this way, potential threat items may be identified, for example, when it is determined that sufficient information exists in the image from which to accurately assess whether threat items are present. It may be appreciated that the image(s) in which an occlusion region is identified may be the same image(s) from which the orientation of the object was determined and/or the image(s) from which an occlusion region is identified may be different than the image(s) from which the orientation of the object was determined. Moreover, while specific reference may be made herein to identifying occlusion regions in a projection image, the image(s) in which an occlusion region is identified may be two-dimensional and/or three-dimensional images. Moreover, images may be radiation images and/or other images, such as optical images, that can be derived from detected radiation, for example.

It may be appreciated that the threat determiner 500 may be configured to identify occlusion regions in the same (projection) image that is utilized for determining the orientation of the object and/or in a different (projection) image representative of the same object. For example, in one embodiment, the object orientation analysis, the identification of an occlusion region, and object recognition analysis may be performed on an image depicting a top-down view of the object. In another embodiment, the object orientation analysis may be performed on an image depicting a top-down view of the object (e.g., depicting an object plane substantially parallel to a plane of the object support) while the identification of an occlusion region and/or object recognition analysis may be performed on an image depicting a side view of the object (e.g., depicting an object plane substantially perpendicular to a plane of the object support). Thus, it may be appreciated that, to the extent practical, a first image utilized to determine an orientation of the object and a second image utilized to generate a segmented object, for example, may be the same image and/or may be different images representative of the same object (e.g., from different views), for example.

The threat determiner 500 comprises, among other things, a segmentation component 502, a feature extraction component 504, and a shield alarm component 506. It may be appreciated that for purposes of the instant application, merely components utilized to identify an occlusion region are illustrated and described herein. Thus, the threat determiner 500 may comprise additional and/or different components if the threat determiner 500 is further configured to perform object recognition analysis or other analysis, for example. By way of example, in one embodiment, the threat determiner 500 may further comprise a comparator configured to compare one or more features of a sub-object (e.g., as represented in the image) to known features of potential threat items to determine if the sub-object is a potential threat item.

The segmentation component 502 is configured to segment the image received by the threat determiner 500 (e.g., from the image reconstructor 124 and/or the orientation component 126 of FIG. 1) to generate a segmented image. That is, stated differently, the segmentation component 502 is configured to use analytical, iterative, and/or other object segmentation techniques to segment or separate the image into a plurality of parts according to defined segmentation parameters. Typically, the segmentation parameters are configured to isolate or locate a potential occlusion region. Thus, via the segmentation, one or more regions of the image that are representative of a potential occluded object may be differentiated from other portions of the image in the segmented image. By way of example, in one embodiment, pixels that are not representative of a potential occlusion region may be zeroed out or otherwise discarded such that the segmented image depicts merely the potential occlusion region. In another embodiment, the pixels that are not representative of a potential occlusion region may be labeled differently than pixels indicative of a potential occlusion region as opposed to being discarded, for example.

It may be appreciated that numerous segmentation techniques are contemplated for use herein. For example, segmentation may comprise, among other things, an erosion technique, a connected component labeling (CCL) technique, and/or a constant false alarm rate (CFAR) technique. Respective segmentation techniques are typically associated with a set of segmentation parameters that guide the segmentation. By way of example, respective pixels (e.g., or voxels in the case of a three-dimensional image) may be associated with one or more different types of properties (e.g., CT score, Compton score, z-effective, material property, etc.) that are derivable from the measured attenuation, and the segmentation parameters may specify, among other things, the type of property to utilize for performing segmentation analysis. Moreover, segmentation parameters may provide threshold values that define a boundary between pixels associated with a potential occlusion region and pixels not associated with a potential occlusion region. By way of example, pixels comprising a density value above a density threshold specified in the segmentation parameters may be labeled as associated with a potential occlusion region and pixels comprising a density value below the density threshold may be labeled as not associated with the potential occlusion region. CCL analysis may then be performed on the pixels labeled as associated with the potential occlusion region to group one or more pixels into a set of pixels (e.g., which are indicative of an occluded object or objects represented in the image).

In one embodiment, one or more of the segmentation parameters may be dynamically adjusted/modified as a function of (e.g., based at least in part upon) the determined orientation of the object. That is, stated differently, the threat determiner 500 may receive information regarding the determined orientation of an object under examination, and the segmentation component 502 may adjust the segmentation parameters such that the segmentation parameters that are utilized when a first image, representative of a first object, is segmented are different than the segmentation parameters that are utilized when a second image, representative of a second object that is oriented differently than the first object, is segmented. By way of example, the type of property and/or the thresholds (e.g., value of a property) may be adjusted as a function of the orientation of the object represented in the image. By way of example, the density threshold utilized for determining whether to label a pixel as associated with a potential occlusion region may be different if the longitudinal axis of the object is angled at 45 degrees relative to the direction of translation than if the longitudinal axis of the object was parallel to the direction of translation.

The example threat determiner 500 further comprises a feature extraction component 504 configured to identify and/or extract, from the segmented image generated by the segmentation component 502, one or more features of the potential occlusion region using feature extraction techniques. By way of example, the average gradient for pixels representing the potential occlusion region and/or a histogram of such pixels may be computed. Just as the segmentation component 502 basis the segmentation on one or more segmentation parameters, the feature extraction component 504 may identify one or more features based at least in part upon one or more feature extraction parameters. For example, such feature extraction parameters may specify which technique to utilize for identifying/extracting features, may specify which type(s) of properties associated with the pixel to utilize when performing the feature extraction technique, and/or feature extraction thresholds (e.g., defining a boundary delineating features and/or for determining whether sufficient criteria has been met to consider a feature as having been identified).

In one embodiment, one or more of the feature extractions parameters may be dynamically adjusted/modified as a function of (e.g., based at least in part upon) the determined orientation of the object. That is, stated differently, the threat determiner 500 may receive information regarding the determined orientation of an object under examination, and the feature extraction component 504 may adjust one or more of the feature extraction parameters such that the feature extraction parameters that are utilized when features are identified in a first segmented image, representative of a first object, are different than the feature extraction parameters that are utilized when features are identified in a second segmented image, representative of a second object that is oriented differently than the first object. By way of example, the algorithm(s) utilized to perform feature extraction, the type(s) of property utilized by the algorithm, and/or the feature extraction threshold(s) may be adjusted/changed as a function of the orientation of the object as determined by an orientation component. For example, the feature extraction component 504 may be configured to adjust a threshold related to the average radiation attenuation of segmented pixels as a function of the determined orientation of the object (e.g., where a group of segmented pixels having an average attenuation above the threshold may be treated differently than a group of segmented pixels having an average attenuation below the threshold).

The example threat determiner 500 further comprises a shield alarm component 506 configured to identify an occluded sub-object represented in the potential occlusion region by comparing at least one of the features identified by the feature extraction component 506 to one or more discrimination parameters. That is, stated differently, at least one identified feature is compared to one or more discrimination parameters to determine whether the potential occlusion region is an occlusion region. For example, the average gradient of pixels (or voxels) comprised within the potential occlusion region may be compared to a discrimination threshold and if the average gradient is exceeds the discrimination threshold, the potential occlusion region may be identified as an occlusion region. It may be appreciated that the discrimination parameters utilized for identifying/confirming an occlusion region may be a function of the type of properties identified/extracted by the feature extraction component 504. For example, the discrimination parameters utilized when the average gradient of pixels within the potential occlusion region is computed may be different than discrimination parameters utilized when a histogram is computed by the feature extraction component 504, for example.

In one embodiment, one or more of the discrimination parameters may be dynamically adjusted/modified as a function of (e.g., based at least in part upon) the determined orientation of the object. That is, stated differently, the threat determiner 500 may receive information regarding the determined orientation of an object under examination, and the shield alarm component 506 may adjust one or more of the discrimination parameters such that the discrimination parameters utilized for identifying/confirming an occlusion region in a first image, representative of a first object, are different than the discrimination parameters utilized for identifying/confirming an occlusion region in a second image, representative of a second object that is oriented differently than the first object. By way of example, a discrimination threshold may be increased or decreased based at least in part upon the determined orientation of the object represented in an image being analyzed by the threat determiner 500.

In one embodiment, the shield alarm component 506 is configured to issue an alert to a terminal (e.g., 130 in FIG. 1), for example, when an occlusion region is identified and/or to issue a notice to other components of the threat determiner 500 to not proceed with further object recognition analysis. That is, stated differently, an occlusion region is indicative of a region of an image where there is insufficient information from which to accurately assess potential threats (e.g., or otherwise assess a grouping of pixels, voxels, etc.). As such, when an occlusion region is identified, automatic object recognition may cease on the image and an alert may be issued by the shield alarm component 506 to notify security personnel, for example, to perform a manual (e.g., visual, hands on, etc.) inspection of the object. Alternatively, in a CT context, the threat determiner 500 may request a second image, depicting the same object from a different viewpoint, and the process may be repeated to determine if an occlusion region is present in the second image that precludes automatic object recognition from being performed, for example.

Figure 6:
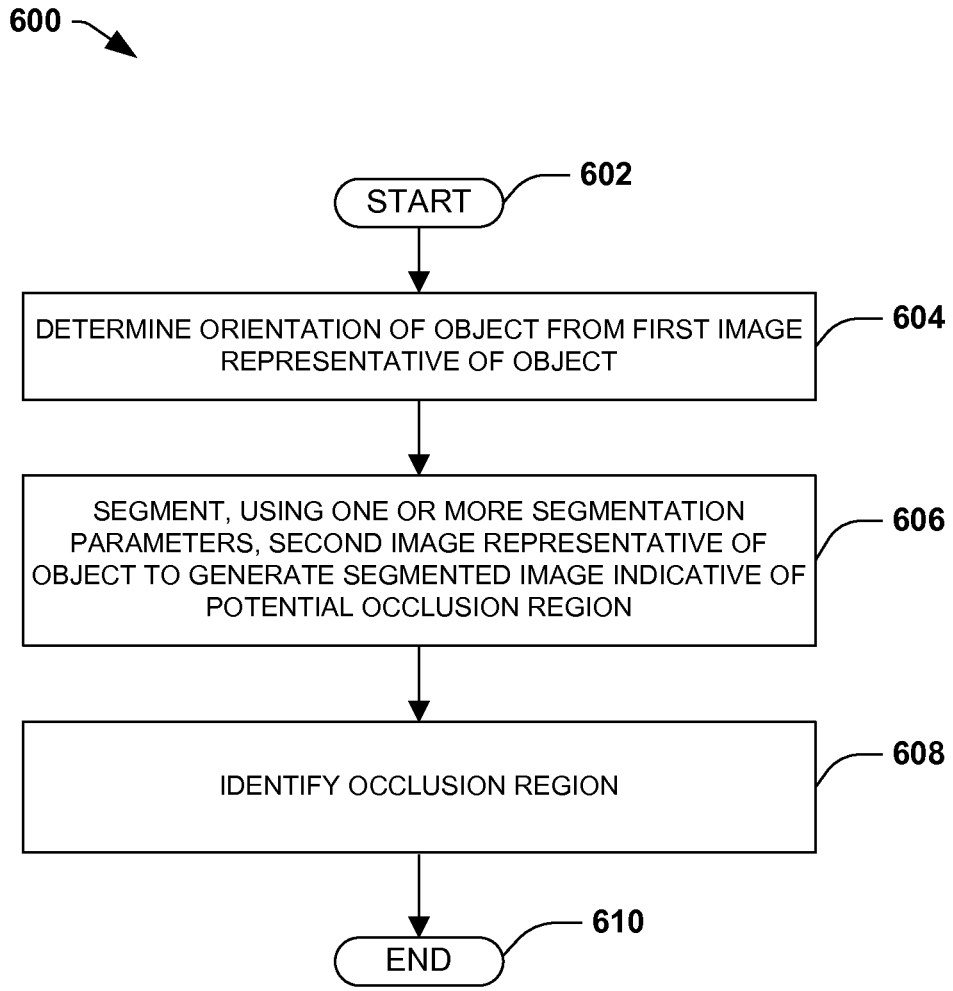
FIG. 6 illustrates a flow diagram of an example method for segmenting an image to identify a potential occlusion region in the image.

FIG. 6 illustrates an example method 600 for segmenting an image to identify a potential occlusion region in an image of an object subjected to examination via a radiation imaging modality, such as a CT system and/or a projection system, for example. In this way, it may be determined whether sufficient information is known about the object from the image prior to (more advanced steps of) object recognition being performed. It may be appreciated that such acts are merely example acts and that the process for automatically identifying/recognizing objects represented in an image(s) may comprise additional and/or different acts than those described herein.

The example method 600 begins at 602 and an orientation of an object is determined from a first image representative of the object (e.g., acquired from the radiation imaging modality) at 604. That is, stated differently, as illustrated in FIG. 4, an image of an object may be generated from projection data yielded from an examination (e.g., such as via a CT system), and analytic, iterative, or other techniques for determining an orientation of an object from a two-dimensional image may be utilized to determine the orientation of the object. For example, as described with respect to FIG. 4, in one embodiment, Eigen analysis may be performed on the image (e.g., on pixels comprised in a two-dimensional image or on voxels comprised in a three-dimensional image) to determine principal vectors of the object.

In one embodiment, as part of determining the orientation of the object, a region of interest within an image representative of the object may be identified and pixels (or voxels) outside of the region of interest may be eroded or otherwise discarded from the analysis. That is, pixels (or voxels) of the image that do not represent the object (e.g., but instead represent air, a portion of the object support, etc.) may be ignored to reduce the data analyzed to determine the orientation of the object. Thus, identifying the region of interest may serve to filter out data that is not relevant to the determination regarding orientation of the object, for example.

At 606 in the example method 600, a second image representative of the object may be segmented, using one or more segmentation parameters, to generate a segmented image indicative of a potential occlusion region. It may be appreciated that the second image may be the same image as the first image utilized to determine the orientation of the object and/or it may be a different image, representing a different view of the object, for example. For example, in one embodiment, the first image is a two-dimensional image representing a top-down view of the object and the second image is a two-dimensional image representing a side view of the object. In another embodiment, both the first image and the second image may be top-down views, for example, of the object.

To segment the second image, one or more pixels of the second image are analyzed according to specified segmentation parameters. Such parameters, which may be dynamically adjusted based upon the orientation of the object, may specify, among other things, one or more segmentation algorithms to use to perform the segmentation, the types of properties to compare when performing the segmentation, and/or segmentation thresholds utilized to identify potential occlusions regions in the image and/or to segment potential occlusion regions from regions of the image that are not representative of occluded objects.

At 608 in the example method 600, a potential occlusion region of the segmented image is compared to one or more discrimination parameters to identify an occlusion region. That is, at 608 in the example method 600, the potential occlusion region identified in the segmented image and/or features derived/extracted therefrom, are compared to discrimination parameters to confirm that the potential occlusion region of the segmented image is an occlusion region or to reject it as not being an occlusion region. Such discrimination parameters may specify, among other things, the algorithms for performing the comparison, the features to compare, and/or discrimination thresholds that trigger the confirmation/rejection of a potential occlusion region, for example. Moreover, as described with respect to FIG. 5, at least one of the discrimination parameters, such as a discrimination threshold, may be dynamically adjusted as a function of the orientation of the object represented in an image being analyzed for occlusion regions. By way of example, the discrimination threshold may be less if the object is oriented with its longitudinal axis parallel to the direction of translation than it would be if the object is oriented with its longitudinal axis perpendicular to the direction of translation. Thus, if the same object were examined twice, with its orientation varied between the two examinations, discrimination thresholds (and/or segmentation parameters and/or feature extraction parameters) may be different when an image produced from the second examination is analyzed relative to an image produced from the first examination.

If an occlusion region is identified in an image, an audio and/or visual alert may be issued, for example, notifying an inspector, such as security personnel, that automatic object recognition failed due to an occlusion region (e.g., where insufficient information is present from which to analyze the image for potential threat items). If an occlusion region is not identified in the image, image data representative of the object may be further processed to automatically identify objects, such as potential threat items, represented in the image data. That is, stated differently, if an occlusion region is not identified, object recognition may be performed on image data representative of the object to identify potential threat items, for example, because the image data comprises a sufficient amount of data from which to perform an object recognition analysis.

The example method 600 ends at 610.

Figure 7:
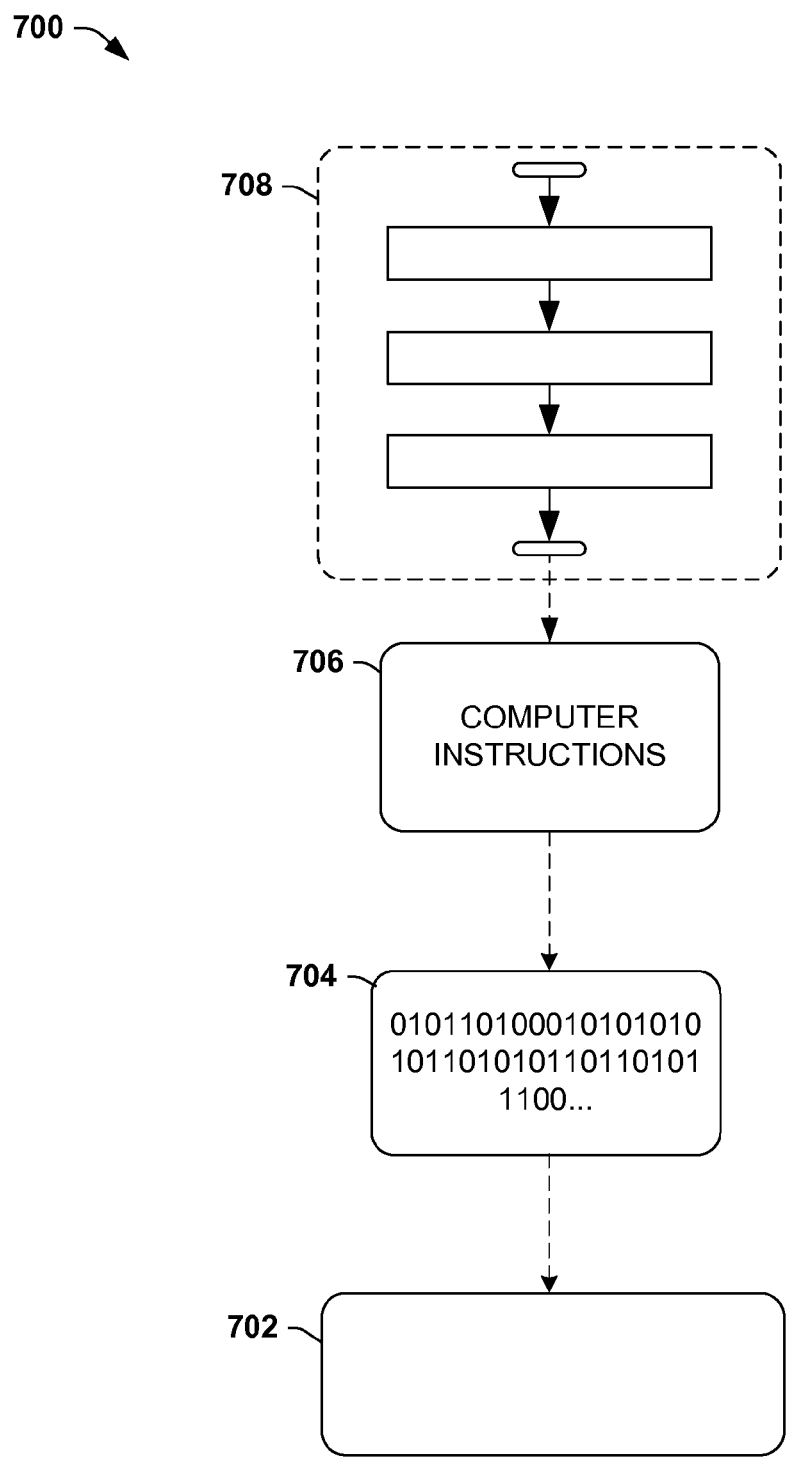
FIG. 7 is an illustration of an example computer-readable medium comprising processor-executable instructions configured to embody one or more of the provisions set forth herein.

Still another embodiment involves a computer-readable medium comprising processor-executable instructions configured to implement one or more of the techniques presented herein. An example computer-readable medium that may be devised in these ways is illustrated in FIG. 7, wherein the implementation 700 comprises a computer-readable medium 702 (e.g., a CD-R, DVD-R, or a platter of a hard disk drive), on which is encoded computer-readable data 704. This computer-readable data 704 in turn comprises a set of processor-executable instructions 706 configured to operate according to one or more of the principles set forth herein. In one such embodiment 700, the processor-executable instructions 706 may be configured to perform a method 708, such as at least some of the example method 600 of FIG. 6. In another such embodiment, the processor-executable instructions 706 may be configured to implement a system, such as at least some of the exemplary environment 100 of FIG. 1 and/or at least some of the example threat determiner (system) 500 of FIG. 5, for example. Many such computer-readable media may be devised by those of ordinary skill in the art that are configured to operate in accordance with one or more of the techniques presented herein.

It may be appreciated that "example" and/or "exemplary" are used herein to mean serving as an example, instance, or illustration. Any aspect, design, etc. described herein as "example" and/or "exemplary" is not necessarily to be construed as advantageous over other aspects, designs, etc. Rather, use of these terms is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims may generally be construed to mean "one or more" unless specified otherwise or clear from context to be directed to a singular form. Also, at least one of A and B or the like generally means A or B or both A and B.

Although the disclosure has been shown and described with respect to one or more implementations, equivalent alterations and modifications may occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated example implementations of the disclosure. Similarly, illustrated ordering(s) of acts is not meant to be limiting, such that different orderings comprising the same of different (e.g., numbers) of acts are intended to fall within the scope of the instant disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes", "having", "has", "with", or variants thereof are used in either the detailed description or the claims, such terms are intended to be inclusive in a manner similar to the term "comprising."

What is claimed is:

1. An imaging apparatus for automatic occlusion detection, comprising:
   a processing unit; and
   memory comprising computer executable instructions that when executed by the processing unit perform operations, the operations comprising:
   generating volumetric data representative of an object, the object resting on a surface during an examination from which the volumetric data is generated;
   projecting the volumetric data onto an object plane parallel to the surface to generate a first two-dimensional image representative of the object;
   determining an orientation of the object from the first two-dimensional image;
   segmenting a second two-dimensional image representative of the object to generate a segmented image based upon one or more segmentation parameters, at least one of the one or more segmentation parameters dynamically adjusted as a function of the orientation of the object;
   identifying, from the segmented image, a potential occlusion region in the second two-dimensional image; and
   identifying one or more features of the potential occlusion region based upon one or more feature extraction parameters, at least one of the one or more feature extraction parameters dynamically adjusted as a function of the orientation of the object.

2. The imaging apparatus of claim 1, the first two-dimensional image different than the second two-dimensional image.

3. The imaging apparatus of claim 1, the second two-dimensional image depicting an object plane substantially perpendicular to the surface.

4. The imaging apparatus of claim 1, the operations comprising:
   identifying an occluded sub-object represented in the potential occlusion region by comparing the one or more features of the potential occlusion region to one or more discrimination parameters, at least one of the one or more discrimination parameters dynamically adjusted as a function of the orientation of the object.

5. The imaging apparatus of claim 1, the determining comprising:
   determining the orientation of the object by performing an Eigen analysis on the first two-dimensional image.

6. The imaging apparatus of claim 1, the determining comprising:
   defining the orientation of the object in terms of Eigen vectors and in terms of a direction of translation of the object during an examination via the imaging apparatus.

7. The imaging apparatus of claim 1, the operations comprising:
   emitting radiation toward the object; and
   detecting radiation that has traversed the object.

8. The imaging apparatus of claim 1, the operations comprising identifying a region of interest within the volumetric data, wherein the projecting the volumetric data comprises projecting merely a portion of the volumetric data representing the region of interest.

9. A method for segmenting an image to identify a potential occlusion region in the image, comprising:
   generating volumetric data representative of an object, the object resting on a surface during an examination from which the volumetric data is generated;

projecting the volumetric data onto an object plane parallel to the surface to generate a first two-dimensional image representative of the object;

performing Eigen analysis on the first two-dimensional image to determine an orientation of the object;

segmenting, using one or more segmentation parameters, a second two-dimensional image representative of the object to generate a segmented image, indicative of a potential occlusion region, at least one of the one or more segmentation parameters dynamically adjusted as a function of the orientation of the object; and identifying one or more features of the potential occlusion region based upon one or more feature extraction parameters, at least one of the one or more feature extraction parameters dynamically adjusted as a function of the orientation of the object, at least one of the generating, the projecting, the performing, the segmenting, the identifying a potential occlusion region, or the identifying one or more features of the potential occlusion region performed at least in part via a processing unit.

10. The method of claim 9, the first two-dimensional image different than the second two-dimensional image.

11. The method of claim 9, dynamically adjusting a segmentation parameter comprising at least one of:
dynamically adjusting a type of property utilized for segmenting the second two-dimensional image, or
dynamically adjusting a value of a property utilized for segmenting the second two-dimensional image.

12. The method of claim 9, comprising identifying an occluded sub-object represented in the potential occlusion region by comparing the one or more features of the potential occlusion region to one or more discrimination parameters, at least one of the one or more discrimination parameters dynamically adjusted as a function of the orientation of the object.

13. The method of claim 12, dynamically adjusting a discrimination parameter comprising at least one of:
dynamically adjusting a type of property utilized for identifying the occluded sub-object, or
dynamically adjusting a value of a property utilized for identifying the occluded sub-object.

14. The method of claim 12, comprising:
identifying an occlusion region of the segmented image by comparing the comparing the one or more features of the potential occlusion region to one or more discrimination parameters; and
issuing an alert when an occlusion region is identified.

15. The method of claim 9, comprising:
performing automatic threat detection on image data representative of the object when no potential occlusion region is identified in the segmented image.

16. The method of claim 9, comprising:
performing a computed tomography (CT) examination of the object to generate the volumetric data.

17. The method of claim 9, the object comprising baggage under examination to identify potential security threats.

18. A non-transitory computer readable medium comprising processor-executable instructions that when executed via a processing unit perform a method for automatic occlusion detection, the method comprising:

generating volumetric data representative of an object, the object resting on a surface during an examination from which the volumetric data is generated;

projecting the volumetric data onto an object plane parallel to the surface to generate a first two-dimensional image representative of the object;

determining an orientation of the object from the first two-dimensional image;

segmenting, using one or more segmentation parameters, a second two-dimensional image representative of the object to generate a segmented image, indicative of a potential occlusion region, at least one of the one or more segmentation parameters dynamically adjusted as a function of the orientation of the object; and identifying one or more features a potential occlusion region based upon one or more feature extraction parameters, at least one of the one or more feature extraction parameters dynamically adjusted as a function of the orientation of the object.

19. The non-transitory computer readable medium of claim 18, the method comprising:
identifying an occluded sub-object represented in the potential occlusion region by comparing the one or more features of the potential occlusion region to one or more discrimination parameters, at least one of the one or more discrimination parameters dynamically adjusted as a function of the orientation of the object.

20. The non-transitory computer readable medium of claim 18, the first two-dimensional image different than the second two-dimensional image.

* * * * *